United States Patent [19]
Nickell et al.

[11] Patent Number: 5,457,274
[45] Date of Patent: Oct. 10, 1995

[54] PINK-FLOWERED, HIGH PROTEIN SOYBEAN PLANTS AND METHODS FOR THEIR PRODUCTION

[75] Inventors: Cecil D. Nickell, Urbana; Paul A. Stephens, Champaign, both of Ill.

[73] Assignee: Research Corporation Technologies, Tucson, Ariz.

[21] Appl. No.: 883,687

[22] Filed: May 15, 1992

[51] Int. Cl.⁶ .............................. A01B 79/00; A01C 1/00; A01H 5/10; A01H 15/00
[52] U.S. Cl. .......................... 800/200; 47/58; 47/DIG. 1; 800/255; 800/DIG. 26
[58] Field of Search ...................................... 800/200, 250, 800/255, DIG. 26; 47/58, DIG. 1

OTHER PUBLICATIONS

Brim, C. A. 1973. Quantitative Genetics and Breeding. *In* Soybeans: Improvement, Production, and Uses. pp. 155–186.
Poehlman, J. M. 1987. Breeding Field Crops. pp. 1987–213.
Woodworth, C. M. (1923) J. Am. Soc. Agron. 15:481–495.
Hartwig, E. E. and Hinson, K. (1962) Crop Sci. 2:152–153.
Stephens, P. A. and Nickell, C. D. (1991) Soybean Genet. Newsl. 18:226–228.
Buzzel, R. I. et al. (1977) Can. J. Genet. Cytol. 19:749–751.
Peters et al. (1984) Crop Sci. 24:237–239.
Bernard (1991) Soybean Genet. Newsl. 18:27–57.

*Primary Examiner*—David T. Fox
*Assistant Examiner*—Erich E. Veitenheimer
*Attorney, Agent, or Firm*—Greenlee and Winner

[57] ABSTRACT

A pink-flowered soybean plant which possesses large seeds and high protein seed content, without a concomitant decrease in yield. The pink-flowered soybean plant is easily distinguished from wild-type and domesticated cultivars by virtue of its unique flower color and appearance. The two commercially significant traits, large seed size and high protein seed content, cosegregate with the pink flower trait. Seed size and protein content of soybean cultivars are therefore efficiently and quickly increased by crossing with the pink-flowered plant, then selecting for pink-flowered progeny. Prior difficulties in tracking and monitoring increases in seed protein content are eliminated.

18 Claims, No Drawings

PINK-FLOWERED, HIGH PROTEIN SOYBEAN PLANTS AND METHODS FOR THEIR PRODUCTION

BACKGROUND OF THE INVENTION

The present invention relates to a novel pink-flowered soybean plant possessing the associated phenotypes of high protein seed content, high yield, and large seeds. A novel soybean plant is disclosed, easily distinguished from wild-type and domesticated cultivars in having a pink flower color. More particularly, this novel pink-flower phenotype is associated with an increased seed size and an increased seed protein content without a concomitant decrease in yield, two attributes of commercial significance. A method of plant breeding, for introducing the pink flower color, increased seed size and increased seed protein traits into domestic cultivars is also disclosed. Further, a process to produce and select for large seeded, high protein soybean varieties, based on this novel flower color, is disclosed.

Soybean (*Glycine max* (L.)) has become an important part of the agricultural economy due to its use as a source of protein. High protein soybean varieties are especially in demand both in the domestic and export markets.

A goal in nearly every soybean improvement program, therefore, is to increase the protein content in the seed. Protein is affected by many genes and can be increased through traditional breeding practices, however improvement will be slow. A minimum of seven years and considerable resources are needed to develop improved varieties. Variety development through normal plant breeding techniques requires constant monitoring of seed protein content, typically with near-infrared reflectance. In addition, protein increase is usually associated with a yield decrease, making it difficult to maintain or increase yield while improving protein content.

Of particular importance to the soybean breeder is the demand for a large seeded, high protein variety. Large seeded soybean varieties are especially desirable for sale to the specialty soybean export market. Large bean size is important, for example, for soybeans used in the manufacture of tofu.

A need therefore exists for a high-yield soybean variety having large seeds and high protein content, and methods for introducing these desired traits into domestic cultivars. A need also exists for a selection method whereby hybrid progeny possessing these desired agronomic traits are readily identified, eliminating the need for constant monitoring of seed protein content.

SUMMARY OF THE INVENTION

It is therefore an object of the present invention to provide a novel soybean variety exhibiting the combined phenotypes of large seed size, high protein seed content and high yield. Unexpectedly, the soybean plants of the present invention generate elevated levels of seed protein, without the generally associated decrease in yield.

It is another object of the present invention to provide a large seeded, high protein, high yield soybean variety which is easily distinguished, on the basis of flower color, from other soybean varieties. The present invention is based in part on the recognition that these desired agronomic traits, large seed size and increased protein content, co-segregated with a novel flower color.

It is a further object of the present invention to provide a large seeded, high protein, high yield soybean plant which exhibits the novel, pink flower phenotype.

It is yet another object of the present invention to provide new soybean plants that can be used efficiently to produce parent lines and hybrids possessing desirable agronomic traits.

The present invention also comprises a process for breeding the novel pink flower color, enhanced seed size, and increased seed protein traits into wild-type soybeans and domestic cultivars.

Finally, the present invention comprises a practical and efficient method for producing and selecting for large seeded, high protein, high yield soybean varieties, based on the novel pink flower color. A soybean breeder can increase seed size and protein content efficiently and quickly by crossing with the pink flowered soybean variety of the present invention, then selecting for plants with pink flowers.

In accomplishing the foregoing objects, there has been provided, in accordance with the present invention, a pink-flowered soybean line which has an increased seed protein content of approximately 1.5 percentage points, relative to the normal seed protein content of commercial cultivars.

There has also been provided in accordance with the present invention a pink-flowered soybean line which has an increased seed size of approximately 25%, relative to the normal seed size of commercial cultivars.

The breeding and selection methods described herein are applicable to all soybean varieties, including wild-type and commercial cultivars. The pink flower phenotype is controlled by a single recessive gene, which segregates according to normal Mendelian genetic principles. Therefore, conventional plant breeding techniques may be used to introduce the phenotypes of enlarged seed size and increased seed protein into any soybean variety using the novel flower color as a marker. The present invention is exemplified by its application to soybean (*Glycine max*); however, its operating principles may be applied to other species of soybean. The invention is not limited to any particular soybean cultivar, but may be applied generally to any plant variety of the genus Glycine, whether wild, domestic or hybrids of the two. The term soybean is used herein to denote the species *Glycine max* and all domestic cultivars thereof.

Other objects, features, and advantages of the present invention will becomes apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

For the purposes of the present description, the terms "cultivar" and "variety" are used synonymously to refer to a group of plants within a species (e.g., *Glycine max*) which share certain constant characters that separate them from the typical form and from other possible varieties within that species. While possessing at least one distinctive trait, a variety is also characterized by a substantial amount of overall variation between individuals within the variety, based primarily on the Mendelian segregation of traits among the progeny of succeeding generations. A "line," as distinguished from a "variety," denotes a group of plants which display less variation between individuals, generally (although not exclusively) by virtue of several generations of self-pollination. In addition, a "line" is defined, for the purpose of the present invention, sufficiently broadly to include a group of plants which carry a mutation for a particular trait, specifically the pink flowered trait as disclosed herein.

As used herein, the terms "co-segregate," "hybrid," "crossing," "recovering progeny," and "selfing," refer to their conventional meanings as understood in the art (see, for instance, Knowles, P. F. and F. N. Briggs, *Introduction to Plant Breeding* (Reinhold Publication Corp., New York, N.Y., 1967). "Substantial" is defined as statistically significant.

Most soybean cultivars have either purple or white flowers. Woodworth, C. M. (1923) "Inheritance of Growth Habit, Pod Color, and Flower Color in Soybeans," J Am. Soc'y Agron 15:481–495. Hartwig, E. E. and K. Hinson (1962) "Inheritance of Flower Color in Soybeans," Crop Sci. 2:152–153, described dilute-purple and near-white flowers, but these flowers appear white and identification requires close examination of the separated standard. In addition, Buzzel, R. I., et al. (1977) "Inheritance and Linkage of a Magenta Flower Gene in Soybeans," Can. J. Genet. Cytol. 19:749–751, report a magenta flower color mutant.

A description of a new flower color, denoted as pink, is presented by Stephens, P. A. and C. D. Nickell (1991) "A Pink Flower Color Mutant in Soybean," Soybean Genet. Newsl 18:226–228, This pink flower was first observed during the summer of 1989 in two F4:5-derived plant rows (designated LN89-5320 and LN89-5322) segregating for purple and pink flower pigmentation while homozygous for gray pubescence and imperfect black hilum. These lines had originated from the cross ('Sherman' x 'Asgrow A2943') x 'Elgin 87'. All F4 plant selections from this cross were purple in flower color. For the two F4:5 plant rows having the pink flower mutation, F5 plants in both rows were classified as pink or purple in flower color, harvested individually, and planted in the spring of 1990. To determine if the pink flower trait is different in appearance from known color genes, pink flowered plants were planted alongside 'Clark' and 'Harosoy' flower color isolines (Bernard, 1978; Table 2).

The pink flower color disclosed herein is quite distinct from all previously reported flower colors. Pink flowers are uniform in color throughout the petals, in contrast to purple, magenta, dilute-purple, and near-white flowers which have increased pigmentation in the veins when compared to the interveinal areas. "Pink" flowers, as used herein, refers to soybean flowers which appear pink in color and uniform in pigmentation throughout the petals, as distinguished from the soybean flowers of known varieties.

The novel soybean plant of the present invention exhibits, among other things, a unique flower color. The gene controlling the pink flower trait is not allelic to any of the known flower color genes. Flower color segregation data for $F_2$ plants demonstrates that the pink flower trait is novel, is not linked to other flower color genes, and is not influenced by cytoplasm (Table 5). Segregation data for selfed progeny indicates that the pink flower trait is controlled by a single recessive gene (Table 3). Selfed progeny from ten heterozygous rows, classified as segregating 3:1 (purple:pink) for flower color (Stephens and Nickell, .Supra), segregated 5:3 (purple:pink) as expected for single recessive gene inheritance. When this pink-flowered plant was crossed with all reported flower color genes and $F_2$ populations classified for flower color (Table 5), results indicated that the pink flower gene was independent of known flower color genes and acted as a modifier gene to decrease pigment expression at the W1 locus, required for purple flower pigmentation, thereby reducing normal purple pigmentation to pink (Stephens and Nickell, supra). The pink flower gene thus interacts with other flower color genes to dilute the intensity of their expression. As used herein, the gene symbol wp means pink flower color inheritance.

As noted above, the pink flowered soybean plant of the present invention was crossed with all known flower color genes and the $F_2$ generation classified according to flower color. The results are shown in Table 5. When W1-wpwp is in combination with wmwm (magenta) the phenotype appears pink, in combination with W3-w4w4 (purple-throat) the phenotype appears near-white, and in combination with w3w3w4w4 (near-white) the flowers appear white. This interaction is demonstrated in the three gene segregation model for the cross LN89-5322-2 X L70- 4422. Contributing to the theoretical 6/64 near-white class are 3/64 W3-w4w4wpwp individuals which are phenotypically difficult to distinguish from the 3/64 w3w3w4w4Wp individuals, and the 1/64 white class appears due to the w3w3w4w4wpwp combination.

The novel soybean line of the present invention is further distinguished from other soybean varieties on the basis of hypocotyl pigmentation. Hypocotyl and flower color pigmentation are closely associated (Hartwig and Hinson, supra). Soybean plants having purple and magenta flowers have purple hypocotyls, and purple-throat types have dilute-purple hypocotyls. The other flower color types, including pink, lack purple pigmentation in the hypocotyl when grown under a 14 hour photoperiod. Anthocyanin malvidin is the predominant pigment responsible for purple coloration in the hypocotyls and is the final product in the anthocyanin pathway (Peters, D. W., et al. (1984) "Hypocotyl Pigments in Soybeans," Crop Sci. 24:237–239). The pink phenotype therefore likely represents a change in the anthocyanin production pathway resulting in a lower level of pigment intensity.

In addition to the unique pink flower color, the novel soybean plant of the present invention possesses high protein seed content, high yield, and large seeds. Seed size and protein content have not been previously found to be associated, and association of flower color with agronomic traits has never been reported. It is interesting and most surprising, therefore, to note that the two agronomic traits identified herein, large seed size and high protein seed content, co-segregate with the novel pink flower trait. The association of these two traits with pink flower color creates a unique situation where the plant breeder can select for improved soybean varieties based on flower color. A primary advantage of the present invention is therefore the ease with which plant breeders can follow the pink flower trait, along with the associated increases in seed size, protein content, and yield.

It is further surprising and unexpected that the increased seed protein content, associated with the pink flower trait of the present invention, it not accompanied by a decrease in yield. Protein increase is usually associated with a yield decrease, making it difficult to maintain or increase yield while improving protein content. Thus, the discovery that these two phenomena are not synchronous with respect to the pink-flowered soybean represents yet another advantage of the present invention.

Soybean varieties possessing specific, desirable traits are often developed by traditional plant breeding techniques. Two cultivars are typically selected for particular traits and then interbred, one cultivar being employed as male and the other as female. After the first cross, the $F_2$ generation plants are normally screened for the traits of interest. Seeds are saved from the $F_2$ plants selected and subsequent generations are grown up, again selecting desirable plants from each generation. In the case of variety development for increased seed protein, a minimum of seven years and considerable resources are needed to develop improved varieties. Protein content must be constantly monitored by analyzing the seed, typically with near-infrared reflectance. In addition, yield decrease is usually associated with a protein increase, making it difficult to maintain or increase yield while improving protein content.

A large seeded, high protein soybean plant possessing the novel pink flower color has been isolated and identified. Progeny plants (designated LN89-5320 and LN89-5322) possessing the pink flower color were selected and their seeds analyzed for both size and protein content. The seed produced by the pink-flowered progeny possess a 25% increase in size and a 1.5 percentage point increase in protein content relative to their purple-flowered counterparts (Table 1). Protein percentage is the percent by weight of the total dry weight of the seed, as measured by near-infrared reflectance. Seed size is measured in cg, based on the average seed weight of a 100 seed sample.

A pink-flowered plant was crossed with each of the five Clark flower color isolines (Bernard, R. L. (1978) "Notice of Release of Clark and Harosoy Isolines," Soybean Genet. Newsl. 1:66–75). A pink-flowered, gray pubescence plant served as the female while Clark isolines were used as the male parent. Although the pink-flowered plant was employed as the female, the Clark isolines could have been employed as the female and the pink-flowered plant could have served as the male. The present invention encompasses these alternative possibilities.

Progeny plants possessing the pink flower color are selected and their seeds analyzed for both size and protein content. The seed produced by the pink-flowered progeny retain the desired traits, i.e., a 25% increase in size and a 1.5 percentage point increase in protein content. The pink-flowered soybean line of the present invention is used efficiently to produce parent lines and hybrids possessing the desired agronomic traits.

The breeding and selection methods described herein are applicable to all soybean varieties, including wild-type and commercial cultivars. The pink flower phenotype is controlled by a single recessive gene, which segregates according to normal Mendelian genetic principles. Conventional plant breeding techniques can therefore be used to introduce the phenotypes of large seed size and high protein seed content into any soybean variety. Thus, by conventional plant breeding techniques, the ordinary artisan can cross a pink-flowered soybean plant with any variety to produce a soybean line possessing the desired phenotypes. The present invention is exemplified by its application to soybean (*Glycine max*); however, its operating principles may be applied to other species of soybean. The invention is not limited to any particular soybean cultivar, but may be applied generally to any plant variety of the genus Glycine, whether wild, domestic or hybrids of the two. Although the instant invention is applicable to all soybean varieties, the breeding and selection methods are preferably carried out by crossing the pink-flowered soybean line with varieties possessing other valuable agronomic traits, including varieties specifically adapted to the particular climate area. Soybean varieties are widely available in commerce from several manufacturers, providing progenitor strains suitable for all climate conditions.

The present invention thus provides a practical and efficient method for producing and selecting for large seeded, high protein, high yield soybean plants, based on the characteristic pink flower color. A soybean breeder can increase seed size and protein content efficiently and quickly by crossing with the pink flowered soybean line of the present invention, then selecting for plants with pink flowers. The pink-flowered soybean plant produced by the novel breeding process is a part of this invention. The seeds and progeny plants produced by crossing with the pink-flowered soybean line are also a part of this invention.

Specific aspects and features of the present invention will become more clear from consideration of the following examples which are set forth to further illustrate the principles of the invention and are not intended, in any way, to be limitative thereof.

EXAMPLES

EXAMPLE 1 Soybean Breeding and Selection Methods

The desired phenotypes of the novel pink-flower soybean, i.e., large seed size and high protein seed content, are transferred to other wild-type or commercial cultivars by conventional plant breeding methods to achieve a new variety combining these desired phenotypes with other valuable agronomic traits. A soybean plant possessing the pink flower trait is crossed, for example, with a variety specifically adapted to the particular climate area.

The desired wild-type soybean, commercial cultivar, or hybrid thereof is crossed by conventional plant breeding methods with a soybean plant having the pink flower phenotype. Breeding methods used in accordance with the present invention include, for example, methods described in Knowles, P. F. and F. N. Briggs, *Introduction to Plant Breeding* (Reinhold Publication Corp., New York, N.Y., 1967), incorporated herein by reference, or any like methods known in the art. Hybrid progeny exhibiting the pink flower trait are selected; seeds from these hybrid progeny will have increased size and protein content. Thus, the seed size and protein content of any soybean variety is efficiently and quickly increased by crossing with the pink flowered soybean line, then selecting for pink flowers.

Seeds of *Glycine max* LN89-5322-1, LN89-5322-2 and LN89-5322-3 were deposited with the American Type Culture Collection (ATCC), Rockville, Md. Seeds of *Glycine max* LN89-5322-2 were deposited on Oct. 22, 1993, as ATCC 75579. Seeds of *Glycine max* LN89-5322-1 and LN89-5322-3 were deposited on Apr. 5, 1995, as ATCC 97108 and ATCC 97109, respectively.

EXAMPLE 2 Agronomic Performance of the Pink-Flowered Soybean

Soybean plants described in Stephens, P. A. and C. D. Nickell (1991) "A Pink Flower Color Mutant in Soybean," Soybean Genet. Newsl. 18:226–228, were individually harvested, allowed to mature, and additional seeds were collected. Twelve progeny lines were selected for performance evaluation. Of these twelve lines, several were heterozygous for flower color while others were homozygous for either purple or pink flower color. The cultivars "Kenwood" (Cianzio, S. R., et al. (1990) "Registration of Kenwood Soybean," Crop Sci. 30:1162), "Burlison" (Nickell, C. D., et al. (1990) "Registration of Burlison Soybean," Crop Sci 30:232), and "Resnik" (McBlain, B. A., et al (1990) "Registration of Resnik Soybean," Crop Sci. 30:424–425) were included as standards for a total of 15 entries. Entries were planted in 4-row plots in a randomized complete block design. Each location consisted of two blocks with each entry entered once per block. Plots were 3 m long with a 76-cm spacing between rows. The two center rows were harvested and seed yield was adjusted for 13% moisture. The eight traits studied were (i) yield (Kg ha$^{-1}$), (ii) plant height at harvest (cm), (iii) maturity (date when at least 95% of the plants have mature pod color), (iv) lodging (scored on the basis of 1=all plants erect to 5=all plants prostrate), (v) 100-seed weight (g), (vi) seed quality (on a scale of 1=good to 5=poor), (vii) percentage seed protein, and (viii) percentage seed oil. Protein and oil composition data were collected at the USDA Northern Regional Research Center, Peoria, Ill. To obtain oil and protein percentages of the seeds, two replications from each location were composited, then approximately 7 g of the composited sample was placed in a Thelco forced air oven for 3 hours at 130° C. The seeds were then transferred to 50-g bottles, sealed, and allowed to cool for 1 hour. Samples were then ground in a Varco model MX-228 electric dry-food grinder and returned to the 50-g bottles. The ground meal was analyzed by near-infrared reflectance in a Pacific-Scientific feed-grain analyzer. Prior to sample processing, the analyzer was calibrated with two sealed standards (wheatmeal and soymeal) and a freshly ground soymeal standard.

The following table presents agronomic data on the pink and purple flower soybean lines, compared with two soybean cultivars. It can be seen that the seeds from pink flowered plants show a 25% increase in size and a 1.5 unit increase in protein content relative to their purple counterparts; no statistically substantial decrease in yield is observed with the increased seed protein. It will be understood that the number of additional biochemical and physiological traits associated with the pink flower phenotype is not exhausted by the present data disclosed herein. Therefore, any additional traits found to be associated with the pink flower phenotype is deemed to fall within the scope of the claims.

TABLE 1

Agronomic performance of pink and purple flower soybean lines compared with two soybean cultivars at four locations in Illinois. 1991.

| Entry | Yield kg/ha | rank | Maturity | Lodging(a) score | Height cm | Seed(a) quality score | Seed(b) weight cg | Seed(b) protein % | Seed(b) oil % | Cruse Yield | rank | Urbana Yield | rank | G. City Yield | rank | Dekalb Yield | rank |
|---|---|---|---|---|---|---|---|---|---|---|---|---|---|---|---|---|---|
| (c)LN89-5322-1 PkG | 3520 | 8 | Sept. 13 | 1.9 | 85 | 1.6 | 19.9 | 41.9 | 20.6 | 3907 | 2 | 3607 | 6 | 3720 | 3 | 2940 | 8 |
| (c)LN89-5322-2 PkG | 3733 | 2 | Sept. 12 | 1.6 | 86 | 1.7 | 20.9 | 41.1 | 20.9 | 3607 | 7 | 4313 | 1 | 3667 | 5 | 3460 | 5 |
| (c)LN89-5322-3 PkG | 3560 | 6 | Sept. 13 | 1.7 | 84 | 1.7 | 20.1 | 41.6 | 20.5 | 3520 | 8 | 3767 | 5 | 3690 | 4 | 3393 | 6 |
| Burlison | 3907 | 1 | Sept. 8 | 1.1 | 74 | 2.0 | 19.2 | 42.6 | 19.5 | 4073 | 1 | 4000 | 3 | 3633 | 6 | 4047 | 1 |
| (d)LN89-5322-6 PG | 3733 | 2 | Sept. 10 | 1.7 | 89 | 1.6 | 16.9 | 39.9 | 21.3 | 3820 | 4 | 3913 | 4 | 3627 | 7 | 3707 | 2 |
| (d)LN89-5322-11 PG | 3533 | 7 | Sept. 11 | 1.7 | 87 | 1.4 | 16.1 | 40.6 | 20.6 | 3773 | 6 | 3380 | 8 | 3807 | 1 | 3293 | 7 |
| (d)LN89-5320-5 PG | 3680 | 4 | Sept. 10 | 1.7 | 83 | 1.6 | 15.9 | 39.5 | 20.8 | 3793 | 5 | 4120 | 2 | 3440 | 8 | 3487 | 4 |
| Kenwood | 3660 | 5 | Sept. 9 | 1.5 | 84 | 1.9 | 14.8 | 38.5 | 21.1 | 3840 | 3 | 3593 | 7 | 3747 | 2 | 3580 | 3 |
| Average | 3666 | | Sept. 11 | 1.6 | 84 | 1.7 | 17.9 | 40.7 | 20.6 | 3792 | | 3837 | | 3665 | | 3488 | |
| LSD (.05) | 327 | | 2 | ns | 5 | 0.3 | 2.0 | 1.3 | 0.7 | 533 | | 720 | | 433 | | ns | |
| CV % | 9.2 | | 0.2 | 30.8 | 5.7 | 15.5 | 5.2 | 1.5 | 1.7 | 6.6 | | 8.8 | | 5.7 | | 11.7 | |
| Burlison | 3907 | | Sept. 8 | 1.1 | 74 | 2.0 | 19.2 | 42.6 | 19.5 | 4073 | | 4000 | | 3633 | | 4047 | |
| Kenwood | 3660 | | Sept. 9 | 1.5 | 84 | 1.9 | 14.8 | 38.5 | 21.1 | 3840 | | 3593 | | 3747 | | 3590 | |
| (e)LN89-5322-2 PkG | 3733 | | Sept. 12 | 1.6 | 86 | 1.7 | 20.9 | 41.1 | 20.9 | 3607 | | 4313 | | 3667 | | 3460 | |
| Pink (average) | 3604 | | Sept. 12 | 1.7 | 85 | 1.7 | 20.3 | 41.5 | 20.6 | 3678 | | 3896 | | 3689 | | 3264 | |
| Purple (average) | 3649 | | Sept. 10 | 1.7 | 86 | 1.5 | 16.3 | 40.0 | 20.9 | 3796 | | 3804 | | 3624 | | 3496 | |

(a)Score: Lodging is rated at maturity; 1 = all plants erect to 5 = all plants laying flat on soil surface. Seed quality is rated considering the amount and degree of wrinkling, defective seed coat (growth cracks), greenishness, and moldy or rotten seeds; 1 = very good to 5 = very poor.
(b)Average of two locations, Urbana and Dekalb, in Illinois. 1991. Seed weight in cg based on 100 seed sample from each replication. Seed composition is measured on samples submitted to the USDA Northern Regional Research Center, Peoria, IL. A 7 g sample of clean seed is prepared by compositing an equal volume or weight of seed from each replication within a location. Protein and oil percentages (dry weight) are measured using near-infrared reflectance.
(c)Pink flower soybean lines.
(d)Purple flower soybean lines.
(e)Pink flowered soybean line being increased during 1992 for possible release.

EXAMPLE 3 Characterization of the Pink-Flowered Trait in Soybean

Purple and pink-flowered soybean plants described in Stephens, P. A. and C. D. Nickell (1991) "A Pink Flower Color Mutant in Soybean," Soybean Genet Newsl 18:226–2282, were individually harvested. Seeds of these purple and pink-flowered soybean plants were planted alongside "Clark" and "Harosoy" flower color isolines (Bernard, R. L. (1978) "Notice of Release of Clark and Harosoy Isolines," Soybean Genet. Newsl. 1:66–75) for comparison of color and appearance. None of the Clark and Harosoy flower color isolines resembled the pink-flowered soybean. The results of the comparative color evaluation are set out in the Table 2.

TABLE 2

Clark and Harosoy isolines for flower color.

| Designation | Genotype† | Phenotype |
|---|---|---|
| Clark 63 | W1 w3 W4 Wm | purple |
| L70-4422 | W1 W3 w4 Wm | purple throat‡ |
| L68-1774 | W1 w3 w4 Wm | near-white |
| L72-2181 | W1 w3 W4 wm | magenta |
| L69-4776 | w1 w3 W4 Wm | white |
| Harosoy 63 | W1 w3 W4 Wm | purple |
| L72-1078 | W1 W3 w4 Wm | purple throat |
| L72-1138 | W1 w3 w4 Wm | near-white |
| T235 | W1 w3 W4 wm | magenta |
| L64-2139 | W1 w3 W4 Wm | white |

†Lines are homozygous for flower color genotype
‡Purple throat = dilute-purple

Table 3 presents segregation data for flower color. The 16 $F_{4:5}$ purple plants segregated in a 1:2 ratio (homozygous:heterozygous) as expected and the 10 heterozygous rows segregated 3:1 (purple:pink) as expected for single gene inheritance. Segregation for flower color thus confirmed that the pink flower color is controlled by a single gene.

TABLE 3

Combined flower color data for LN89-5320 and LN89-5322.

| | Flower color | | | | Chi square probability |
|---|---|---|---|---|---|
| | purple | seg. no. | pink | Ratio | |
| 1989 plants | 16 (9 + 7)§ | | 7(4 + 3) | 3:1† | 0.55 (0.63, 0.72) |
| 1990 $F_{4:6}$ plant row | 6 | 10 | 7 | 1:2:1‡ | 0.79 |
| 1990 segregation for $F_{4:5}$ purple plants | 6 | 10 | | 1:2 | 0.72 |
| 1990 individual plant data for 10 segregating rows | 350 | | 128 | 3:1 | 0.37 |

†Ratio = purple to pink
‡Ratio = purple to segregating to pink?
§Data in parenthesis for LN89-5322 and LN89-5320 respectively

EXAMPLE 4 Inheritance of Pink Flower in Soybean

To test if the pink flower gene is allelic to the known flower color genes, a pink-flowered plant described in Stephens, P. A. and C. D. Nickell (1991) "A Pink Flower Color Mutant in Soybean," Soybean Genet. Newsl 18:226–228, was crossed to each of the five Clark flower color isolines (Bernard, R. L. (1978) "Notice of Release of Clark and Harosoy Isolines," Soybean Genet Newsl. 1:66–75). Table 4 lists parents used in this study and their flower colors.

TABLE 4

Flower color and Genotype for soybean lines used as parents in crosses.

| Parental line | Flower Color | Genotype† |
|---|---|---|
| LN89-5322-2 | Pink | t W1 w3 W4 Wm wp‡ |
| Clark 63 | Purple | T W1 w3 W4 Wm Wp |
| L70-4422 | Purple-throat§ | T W1 W3 w4 Wm Wp |
| L68-1774 | Near-white | T W1 w3 w4 Wm Wp |
| L72-2181 | Magenta | T W1 w3 W4 wm Wp |
| L69-4776 | White | T w1 w3 W4 Wm Wp |
| Burlison | White | T w1 w3 W4 Wm Wp |

†Each locus is considered homozygous for genes as indicated.
‡T,t = tawny and gray pubescence respectively. W1, W3, W4 and Wm have been previously documented, Wp is our proposed designation.
§Purple-throat = dilute-purple A pink-flowered, gray pubescence plant served as the female while Clark isolines were used as the male parent since they possessed the phenotypic marker, tawny pubescence. A cross was confirmed by an $F_1$ plant having tawny pubescence. To test for cytoplasmic effects, reciprocal crosses were made between the pink-flowered plant and the cultivar "Burlison" (Nickell, C. D., et al. (1990) "Registration of Burlison Soybean," Crop Sci. 30:232) which has white flowers and tawny pubescence.

$F_1$ plants were grown in a greenhouse; harvested $F_2$ seed were grown in the field for flower color classification. Flowers on $F_2$ plants were classified by comparing flower phenotype to flowers on Clark isoline parents. After classification for flower and pubescence color, the plants were labelled with coded plant tags. Plant tags and flower color were periodically reviewed to confirm proper color classification, and additional tags were added to later flowering plants.

Table 5 presents flower color segregation data for the $F_2$ generation. It can be seen that the pink flower trait is novel, is not linked to other flower color genes, and is not influenced by cytoplasm. In addition, a 3:1 (purple:pink) ratio in the $F_2$ generation of LN89-5322-2 X Clark 63 confirms the occurrence of a recessive allele controlling pink flower color. Based on the data in Table 5, the flower color genotype for LN89-5322-2 is W1W1w3w3W4W4WmWmwpwp.

TABLE 5

Soybean plants classified in the F2 generation according to their flower color

| Cross | Alleles Segr. | Total plants | Purple | Magenta no. | Purple-throat | Pink | Near-white | White | Theoretical ratio | $X^2$ | P |
|---|---|---|---|---|---|---|---|---|---|---|---|
| LN89-5322-2xClark 63 | $\frac{wp}{Wp}$ | 125 | 88 | — | — | 37 | — | — | 3:1 | 1.4 | 0.27 |
| LN89-5322-2xL70-4422 | $\frac{w3W4wp}{W3w4Wp}$ | 115 | 60 | — | 21 | 17 | 15† | 2 | 36:9:12:6:1 | 7.3 | 0.13 |
| LN89-5322-2xL68-1774 | $\frac{W4wp}{w4Wp}$ | 129 | 75 | — | — | 20 | 27 | 7 | 9:3:3:1 | 1.2 | 0.81 |
| LN89-5322-2xL72-2181 | $\frac{Wmwp}{wmWp}$ | 123 | 70 | 23 | — | 30 | — | — | 9:3:4 | 0 | 1.00 |
| LN89-5322-2xL69-4776 | $\frac{W1wp}{w1Wp}$ | 111 | 61 | — | — | 15 | — | 45 | 9:3:4 | 3.5 | 0.18 |
| LN89-5322-2xBurlison | $\frac{W1wp}{w1Wp}$ | 124 | 73 | — | — | 21 | — | 30 | 9:3:4 | 0.4 | 0.88 |
| Burlison xLN89-5322-2 | $\frac{w1Wp}{W1wp}$ | 83 | 40 | — | — | 16 | — | 27 | 9:3:4 | 2.8 | 0.27 |

†Since the W3-w4w4wpwp phenotype is light purple throat due to the presence of wp, it cannot be distinguished from near-white and therefore phenotypically becomes part of the near-white class

What we claim is:

1. A soybean plant having pink flowers and uniform pigmentation throughout each petal as a distinguishing phenotype, wherein said plant is selected from the group consisting of ATCC 97108, ATCC 75579 and ATCC 97109.

2. A plant as set forth in claim 1 wherein said plant additionally displays the phenotype of increased seed size as compared to *Glycine max* cv. Kenwood.

3. A plant as set forth in claim 1 wherein said plant additionally displays the phenotype of increased seed protein content as compared to *Glycine max* cv. Kenwood.

4. A plant as set forth in claim 3 wherein the increased seed protein is not accompanied by a substantial decrease in yield.

5. A plant as set forth in claim 1 wherein said pink flower phenotype is conveyed by a recessive gene.

6. A plant as set forth in claim 1 wherein said pink flower phenotype co-segregates with additional phenotypes of increased seed size and increased seed protein as compared to *Glycine max* cv. Kenwood.

7. A plant as set forth in claim 1 having additional phenotypes of seed size and seed protein content wherein said additional phenotypes of said plant co-segregate with said phenotype of pink flowers, in crosses with soybean plants lacking pink flowers, such that an F1 progeny plant of said cross, when selfed yields an F2 progeny plant having pink flowers as a distinguishing phenotype and said F2 progeny plant also displays the additional phenotypes of seed size and seed protein content at least equivalent to the seed size and seed protein content of said plant of claim 1.

8. Seeds produced by the soybean plant of claim 1.

9. A soybean plant descended from a pink-flowered soybean line selected from the group consisting of ATCC 97108, ATCC 75579 and ATCC 97109.

10. The soybean plant of claim 9 wherein said plant has pink flowers and uniform pigmentation throughout each petal as a distinguishing phenotype.

11. The soybean plant of claim 9 wherein said plant, when selfed, will yield a progeny plant having pink flowers and uniform pigmentation throughout each petal as a distinguishing phenotype.

12. A method of soybean breeding using a first parental plant having the phenotype of pink flower color, wherein said plant is selected from the group consisting of ATCC 97108, ATCC 75579 and ATCC 97109 to introduce associated traits into a soybean line comprising the steps of:

(a) crossing said first parental plant with a second parental plant;

(b) recovering F1 hybrid plants;

(c) selfing said F1 hybrid plants;

(d) selecting for F2 hybrid plants having said phenotype of pink flower color; and (e) back-crossing said pink-flowered hybrids recurrently with said first parental plant, thereby producing a soybean line having said phenotype of pink flower color.

13. A method of claim 12 wherein said first parental plant is a plant of the line ATCC 75579.

14. Seeds produced according to the method of claim 12.

15. A progeny plant produced according to the method of claim 12.

16. A soybean plant descended from a first parental plant selected from the group consisting of ATCC 97108, ATCC 75579 and ATCC 97109 and a second parental plant, wherein said plant displays the phenotype of increased seed protein content as compared to the second parental plant.

17. A soybean plant descended from a first parental plant selected from the group consisting of ATCC 97108, ATCC 75579 and ATCC 97109 and a second parental plant, wherein said plant displays the phenotype of increased seed size as compared to the second parental plant.

18. A soybean plant descended from a pink-flowered soybean line selected from the group consisting of ATCC 97108, ATCC 75579 and ATCC 97109 wherein said plant carries the flower color gene wp, and wherein said plant will produce progeny that have pink flowers and uniform pigmentation throughout each petal as a distinguishing phenotype.

* * * * *